United States Patent [19]

Schonberg et al.

[11] Patent Number: 5,418,372

[45] Date of Patent: * May 23, 1995

[54] INTRAOPERATIVE ELECTRON BEAM THERAPY SYSTEM AND FACILITY

[75] Inventors: Russell G. Schonberg, Santa Clara County; Jerome M. Vaeth, Marin County; Mary L. M. Pollaczek, Contra Costa County; Ronald E. Haynes, San Juan County; Stephen E. Haynes, Alameda County, all of Calif.

[73] Assignee: Intraop, Inc., Sunnyvale, Calif.

[*] Notice: The portion of the term of this patent subsequent to Jun. 14, 2011 has been disclaimed.

[21] Appl. No.: 258,569

[22] Filed: Jun. 10, 1994

Related U.S. Application Data

[63] Continuation of Ser. No. 40,115, Mar. 30, 1993, Pat. No. 5,321,271.

[51] Int. Cl.⁶ .............................................. H01J 37/30
[52] U.S. Cl. ................................................. 250/492.3
[58] Field of Search ......................... 250/492.3; 378/65

[56] References Cited

U.S. PATENT DOCUMENTS 5,321,271 6/1994 Schonberg et al. .............. 250/492.3

Primary Examiner—Jack I. Berman
Attorney, Agent, or Firm—Stanley Z. Cole

[57] ABSTRACT

An electron beam therapy system and a facility for using an electron beam therapy system. In the preferred embodiment, the electron beam therapy system comprises a linear accelerator, microwave source, and associated electronics disposed in a housing. The housing is mounted on a positioning means such as a C-arm to direct the electron beam to the desired site on the patient. The entire housing and positioning means is mobile and may be moved to different locations in the facility. Connectors are provided at the different locations in the facility to connect the electron-beam source to a central power source within the facility.

15 Claims, 3 Drawing Sheets

INTRAOPERATIVE ELECTRON BEAM THERAPY SYSTEM AND FACILITY

This application is a continuation of application U.S. Ser. No. 08/040,115, filed on Mar. 30, 1993, having the same title and the same inventors, which issued as U.S. Pat. No. 5,321,271, on Jun. 14, 1994.

This invention relates generally to intraoperative radiation therapy and in particular to a mobile intraoperative electron beam therapy system that can be used in existing surgical suites with minimal or no structural retrofit.

BACKGROUND OF THE INVENTION

Radiation has long been used intraoperatively to treat a variety of cancers by delivering a high local dose of radiation directly to the tumor bed through the operative site. Early intraoperative radiation treatment methods utilized x-rays as the radiation source. More recent intraoperative therapy installations have employed beams of high energy electrons as the radiation source to provide a homogeneous dose of radiation with a rapid falloff in radiation intensity beyond the treatment volume, thereby minimizing exposure of noncancerous tissue to the radiation.

In a typical intraoperative electron beam therapy (IOEBT) procedure, the surgeon removes the bulk of the patient's tumor so that minimal residual disease remains. The attending radiation oncologist selects the electron beam energy and field size required to treat the target volume. A single cancerocidal radiation dose is then delivered to the tumor site, while the dose to normal tissues is kept to a minimum. IOEBT has been shown to be especially useful in the treatment of bone sarcomas, soft tissue sarcomas, bronchogenic, gynecological, colorectal, pancreatic and gastric cancers.

The primary drawbacks of present IOEBT systems are size and weight. Equipment currently available to a clinical facility interested in an IOEBT system is a large, 5–10 ton gantry-mounted linear accelerator, operating at 5 to 20 MeV and requiring a specially-designed operating suite with large amounts of radiation shielding and a weight-bearing floor. The weight of the accelerator itself and the need to provide special shielding and structural support for the IOEBT room virtually guarantees that each IOEBT system will be used in only one specialized shielded theater equipped with a dedicated linear accelerator. This dedicated-facility approach requires a large capital outlay on the part of the hospital. More importantly, from a medical point of view, a separate theater makes treatment of the patient much more difficult.

The drawbacks of this situation arise from the need to transport the patient during surgery from the operating room to the radiation oncology room and include increased risk of infection, increased anesthesia requirements, and increased complexity of OR and radiation therapy schedules to accommodate the use of two rooms for a single surgical procedure.

Orthovoltage x-ray treatment equipment is lighter and requires less shielding than IOEBT systems and therefore avoids some of the logistical problems of the IOEBT approach. However, orthovoltage systems have lengthy treatment times, inhomogeneous dose distributions and high bone absorption. These drawbacks limit the clinical efficacy of orthovoltage as an intraoperative treatment procedure.

What has been needed is an IOEBT system that can be used in one or more existing surgical suites without the addition of extensive radiation shielding and structural support to the operating rooms. This invention meets this need by providing a surgical facility that has multiple operating rooms sharing a single transportable IOEBT system. The invention also provides a mobile IOEBT system having an electron beam source mounted on movable mechanical supports. The IOEBT system is designed to be light enough to avoid the need to add structural support to preexisting medical care facilities. The IOEBT system of this invention requires only minimal additional radiation shielding.

The preferred embodiment of the electron beam therapy system of this invention includes a linear accelerator and microwave power source disposed in an accelerator head housing. The housing is mounted on a movable support that permits orientation of the electron beam applicator tube to the correct position with respect to the patient being treated.

DETAILED DESCRIPTION OF THE PREFERRED EMBODIMENT

A number of interrelated design elements must be considered when placing an IOEBT system in a surgical environment. These design elements include: (1) providing sufficient electron beam energy to meet penetration and dosage requirements; (2) minimizing the size and weight of the accelerator head; (3) providing means for mounting and moving the mechanical support for the accelerator head; and (4) providing adequate shielding for primary x-rays generated by the system as well as for scatter radiation. The preferred embodiment of this invention meets these requirements, in part, by using an X-band microwave accelerator as the electron beam source instead of a conventional S-band accelerator. Notwithstanding that use of an X-band accelerator in the preferred embodiment, it should be understood that this invention can be practiced with an S band accelerator like those commonly used in medical therapy systems. The disadvantage is the weight increase that users will be forced to contend with. Yet such a unit will be functional within the hospital environment. The accelerator, again preferably an X-band unit, and its applicator head are mounted on a mechanical support which serves to accurately place the accelerator head in proper position with minimum hazard to the patient and minimum time requirements for adjustments.

The system also has a beam stopper to intercept primary photons generated either in the accelerator head or in the patient. The beam stopper is matched to the primary beam field size. Additional room shielding is provided as needed for the safety of the surgical team but generally not much shielding (not much more than that used during a catherization procedure) is required.

The IOEBT system of this invention may be used in a dedicated room. Alternatively, a single modulator may be used in to many surgical rooms and the accelerator head, its mechanical support and controls moved from room to room as needed. This will be further described in connection with FIG. 3.

Figure 1:
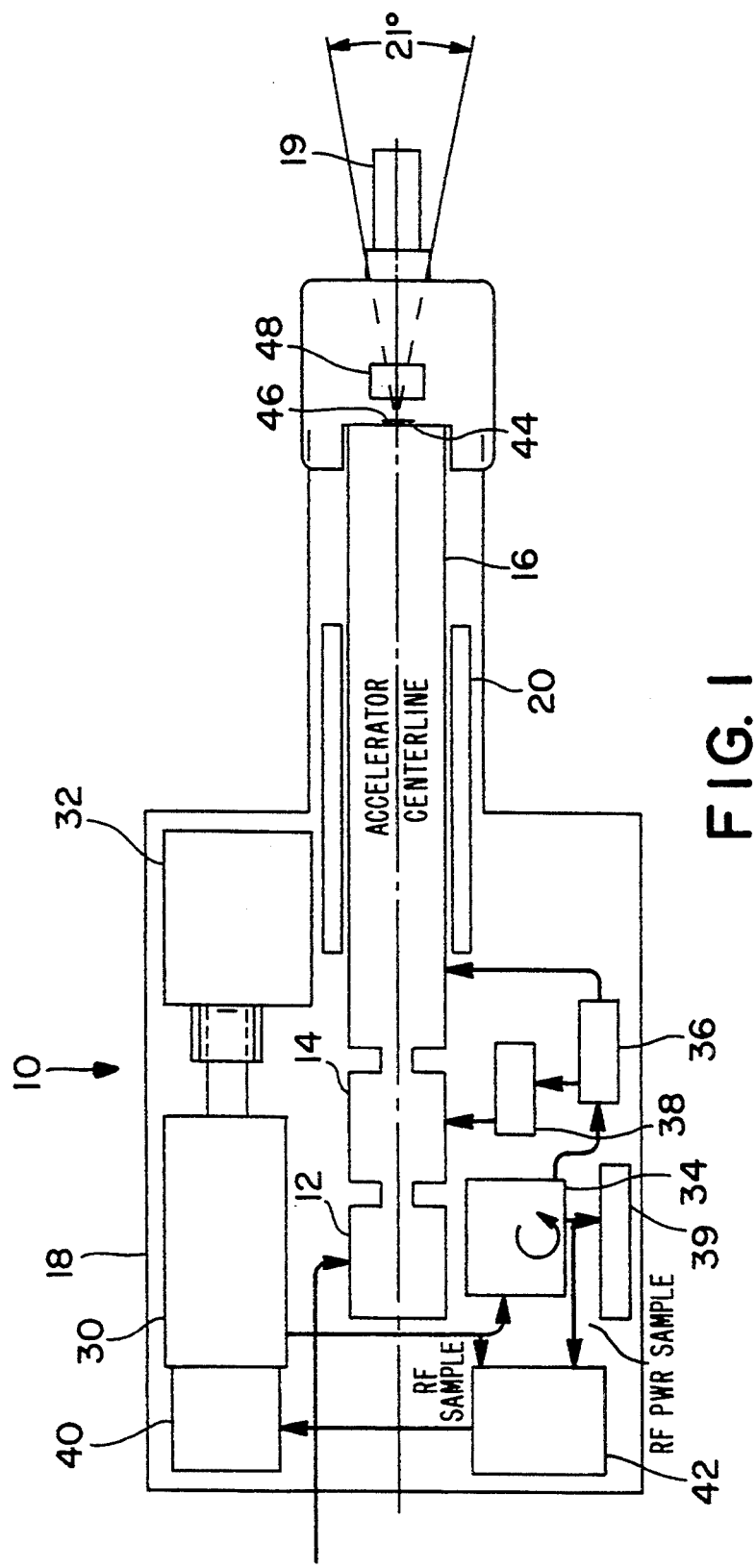
FIG. 1 is a schematic representation of the preferred electron beam source.

The preferred electron beam source for the IOEBT system of this invention is an X-band linear accelerator operating at a peak beam energy of 13 MeV with settings at 6 MeV and 9 MeV. As shown in FIG. 1, the electron beam source comprises accelerator head 10 which includes an electron gun 12, a prebuncher 14, and a series of standing wave cavities 16 disposed along the centerline of housing 18. Electron gun 12 is preferably a Litton M707. The injector cathode of electron gun 12 operates at 40 kV and has a very small diameter emitting surface. This design provides low emittance and good capture efficiency while maintaining a low energy spread. The injector also has a non-interceptor grid to enable accurate control of the injected current. Injected current control makes it possible to (1) monitor the output beam signal and (2) to use a feedback circuit to regulate and adjust the injector current to stabilize the delivered dose.

The dimensions of standing wave cavities 16 vary in order to produce beam bunching, thus reducing energy spread. A solenoid or focusing coil 20 is placed over the accelerating structure to confine the beam and to thereby optimize operation by improving transmission efficiency. A titanium window 44 at the beam outlet maintains a vacuum within the accelerator. Window 44 could also be formed from beryllium. A thin scattering foil 46 at the beam outlet spreads the electrons. In the preferred embodiment, the electrons are scattered over a 20 cm×20 cm treatment field with a maximum of 10% variation in dose rate. A removable treatment cone or application tube 19 is disposed following scattering foil 46 at the beam exit region to define the treatment field size. A variety of applicator tubes of different sizes may be used depending on the treatment desired.

The microwave power necessary to drive the accelerator is generated by a magnetron 30 such as the California Tube Laboratory model VMX 1100. In the preferred embodiment, magnetron 30 is capable of operating at a peak power of 1.5 Megawatts and 1.5 kilowatts of average power, i.e., at a duty cycle of 0.001. The pulse length of the preferred magnetron is 4 microseconds, and the pulse repetition frequency can vary from 50 to 250 pulses per second.

In the preferred embodiment, the system employs a conventional modulator and power supply (not shown) using a hydrogen thyratron switching unit to produce 3 MW peak power for the magnetron via a suitable cable and cable connector. Power to magnetron 30 is converted from 8-9 kV to 35 kV by a pulse transformer 32, also disposed within housing 18. Microwave power from the magnetron is transmitted to prebuncher 14 via a power splitter 36 and a phase shifter 38. The main power is coupled to the standing wave cavities 16 via a four-port circulator 34. Power not absorbed in the accelerator is reflected and shunted into a water-cooled dummy load 39. The dummy load is designed to absorb the complete power generated by the magnetron in the event of a load failure. A DeQuing regulation system is used to maintain a constant pulse level.

The resonant frequency of the magnetron and accelerator must match in order to optimize system operation. This is achieved by using a tunable magnetron, with the tuner driven by a stepper motor 40. The stepper motor is controlled by an automatic frequency control system 42 which detects phase variation between the forward and reflected power applied to the accelerator, thus forming a tracking system to maintain optimum operation irrespective of temperature or load changes.

A transmission chamber 48 at the beam outlet monitors dose rate and integral dose. The chamber is made from plastic elements (preferably Kapton) coated with a thin metallised layer to minimize production of bremsstrahlung x-rays.

Figure 2B:
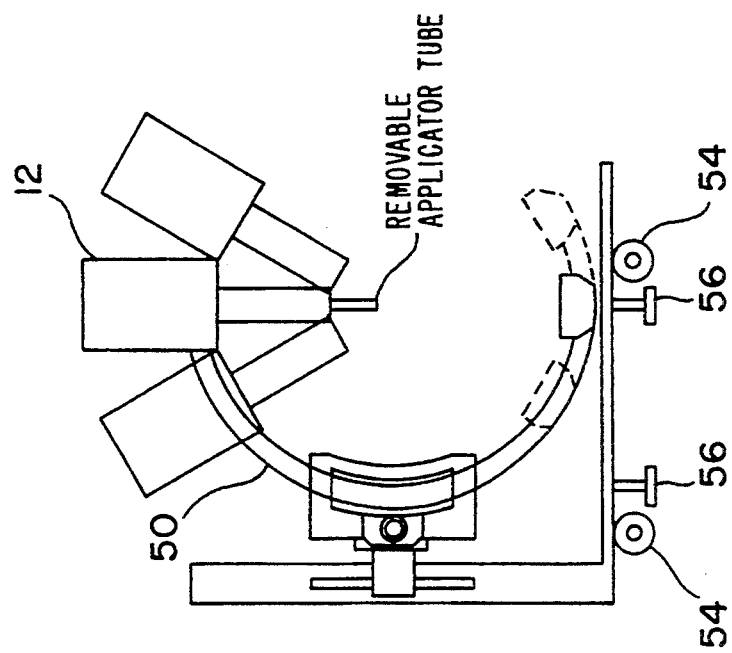
FIG. 2(b) is a side view of the accelerator head mounted in the movable support of FIG. 2(a).
Figure 2A:
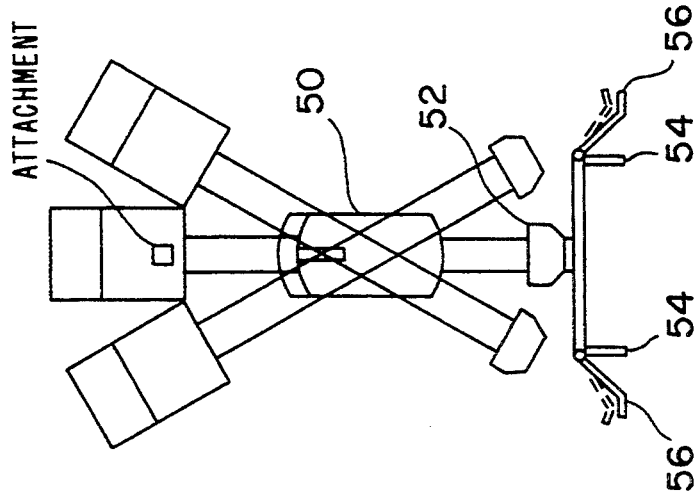
FIG. 2(a) is a front view of the accelerator head mounted in a movable support.

In the preferred embodiment, the accelerator head housing 10 is mounted on a mechanical support or C-arm 50. As shown in FIGS. 2(a) and 2(b), the C-arm can articulate the electron beam source over a series of arcs. In the preferred embodiment, accelerator head housing 10 can rotate ±30° about the "X" and "Z" axes and has a vertical movement of 25 cm. Movement of the accelerator head is controlled by a joystick (not shown) having a proportional speed control.

C-arm 50 has a beam stopper 52 mounted on the side opposite accelerator head housing 10 to intercept the primary x-ray contaminants produced by the scattering foil and collimator. Beam stopper 52 may be formed from lead, tungsten, or any other shielding material. The required size of the beam stopper depends on the maximum field size of the electron beam. In the preferred embodiment, the electron beam field size is set at 15 cm×15 cm. The preferred dimensions for a lead beam stopper are therefore approximately 40 cm×40 cm with a thickness of approximately 20 cm.

To facilitate moving from one operating room to another, C-arm 50 has a set of wheels 54. A set of support feet 56 can be lowered to stabilize C-arm 50 or a braking mechanism set on wheels 54 when the unit is in its desired location.

The IOEBT system of this invention requires a minimal amount of radiation shielding to be added to a pre-existing surgical suite. For example, a wall with a leaded glass window may separate the surgical team from the patient during operation of the IOEBT to protect the medical personnel from any stray radiation. The glass window provides visual monitoring of the patient which can supplement electronic video monitoring.

Modifications to the preferred embodiment will be apparent to those skilled in the art.

In addition, the accelerator head may be ceiling-mounted instead of mounted in the C-arm described above. The accelerator head may be moved from room to room along tracks formed in the rooms' ceilings, or each accelerator head may be dedicated to a single room.

Figure 3:
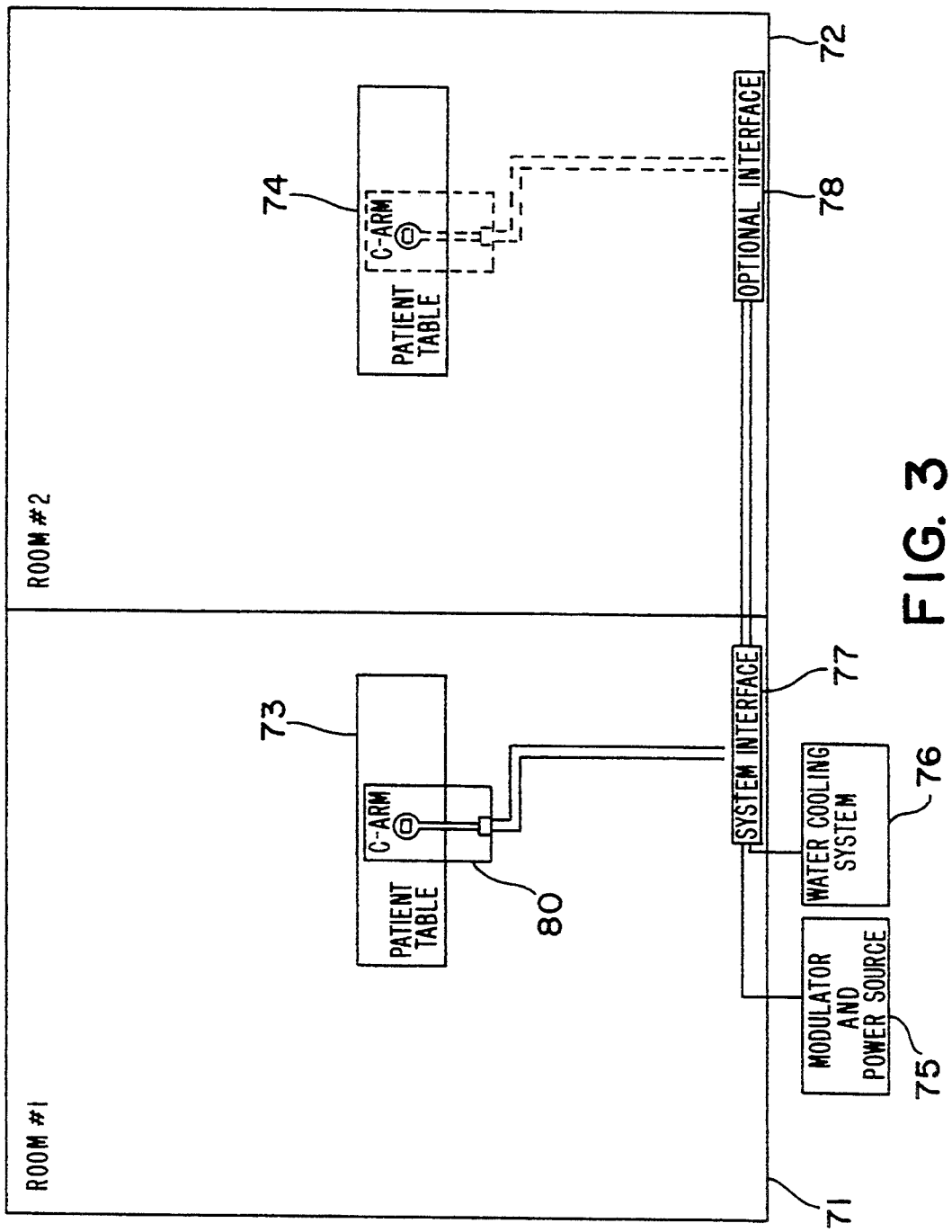
FIG. 3 is a plan view of a layout of a hospital facility in which this invention may be used.

This is illustrated in FIG. 3 which illustrates two operating rooms 71 and 72 each with a patient table 73 and 74. A modulator and power source 75 and a water cooling system 76 are positioned in the walls of the building and of the rooms and feeds to interfaces 77 and 78. In FIG. 3 the intraoperative device 80 of this invention is shown in room 71 connected to room interface 77. A dotted illustration is shown of the intraoperative device 80 in room 72 connected to interface 78. This is how the unit would appear when moved to room 72 for use in this operating theater.

The electron beam sources may be modified in accordance with techniques known in the art, such as by using lead cutouts to shape the electron beam distribution. In addition, the accelerator beam energy may be controlled by operating the system at a single output power level and using beryllium buttons to reduce the electron beam energy to the desired level.

While this invention is particularly useful in treating patients intraoperatively, it may also be used for conventional external radiation therapy, such as the treatment of Karposi's sarcoma. Other modifications to this invention and its intended use will be apparent to those skilled in the art.

We claim:

1. A mobile electron beam therapy system comprising:
    a housing;
    an electron beam source disposed within said housing for generating an electron beam using an s-band linear accelerator; said electron beam source and said linear accelerator being interpositioned so that a generated electron beam exits said linear accelerator collinearly in the direction electrons travel within said accelerator;
    applicator means associated with the housing for directing an electron beam generated by the electron beam source; and
    means for positioning the housing so that the applicator means directs an electron beam generated by the electron beam source in a continuous path in line with said linear beam to a predetermined location in patient treatment.

2. The mobile electron beam therapy system of claim 1 wherein the electron beam source further comprises a microwave source disposed within the housing.

3. The mobile electron beam therapy system of claim 2 wherein the electron beam source further includes a pulse transformer disposed within the housing.

4. The mobile electron beam therapy system of claim 1 wherein the means for positioning comprises means for rotating the housing about a first axis.

5. The mobile electron beam therapy system of claim 4 wherein the means for positioning further comprises means for rotating the housing about a second axis.

6. The mobile electron beam therapy system of claim 5 wherein the means for positioning further comprises means for moving the housing vertically with respect to the patient.

7. The mobile electron beam therapy system of claim 6 wherein the means for positioning comprises a C-arm.

8. The mobile electron beam therapy system of claim 7 further comprising a beam stopper mounted on the C-arm.

9. The mobile electron beam therapy system of claim 1 wherein the means for moving comprises a wheeled mount.

10. The mobile electron beam therapy system of claim 1 further comprising a power source and means for connecting the power source to the electron beam source.

11. The mobile electron beam therapy system of claim 10 wherein the means for connecting comprises a first connector at the first location and a second connector at the second location.

12. An electron beam therapy system comprising:
    a plurality of locations adapted for treating patients with electron beam therapy;
    a mobile electron beam therapy system as described in claim 1;
    means for moving the electron beam source into any of said plurality of locations; and
    means in each room for connecting the electron beam source to a utility source.

13. The electron beam therapy facility of claim 12 wherein the electron beam therapy system comprises a housing and an electron beam source disposed within the housing and wherein said means within each room as a supply for said electron beam source also comprises a cooling system.

14. The electron beam therapy facility of claim 12 further comprising applicator means on the housing for directing an electron beam generated by the electron beam source and means for positioning the housing so that the applicator means directs an electron beam generated by the electron beam source to a predetermined site on a patient.

15. Apparatus in accordance with claim 1 including means to permit easy movement of the housing and the means for positioning together from a first location to a second location.

* * * * *

UNITED STATES PATENT AND TRADEMARK OFFICE
CERTIFICATE OF CORRECTION

| | | |
|---|---|---|
| PATENT NO. | : 5,418,372 | |
| APPLICATION NO. | : 08/258569 | |
| DATED | : May 23, 1995 | |
| INVENTOR(S) | : Schonberg et al. | |

It is certified that error appears in the above-identified patent and that said Letters Patent is hereby corrected as shown below:

Column 6, line 17: change "system" to --facility--

Signed and Sealed this

Thirteenth Day of October, 2009

David J. Kappos
*Director of the United States Patent and Trademark Office*